United States Patent [19]

Dean, Jr. et al.

[11] 4,141,346
[45] Feb. 27, 1979

[54] OCULAR PLETHYSMOGRAPH

[75] Inventors: Robert C. Dean, Jr., Norwich, Vt.;
Paul A. Hoisington; Brian F. Walsh, both of Etna, N.H.; Frank E. Mastro, Lebanon, N.H.

[73] Assignee: Life Sciences, Inc., Greenwich, Conn.

[21] Appl. No.: 766,058

[22] Filed: Feb. 7, 1977

[51] Int. Cl.² .................................................. A61B 5/02
[52] U.S. Cl. ........................................ 128/2 T; 73/80; 128/2.05 V
[58] Field of Search ............. 128/2 T, 2.05 E, 2.05 Q, 128/2.05 V, 2.05 N, 2.05 A, 2.05 B, 2.05 D, 2.05 M; 73/80, 707, 716; 137/462

[56] References Cited

U.S. PATENT DOCUMENTS

| 3,308,810 | 3/1967 | Galin | 128/2 T |
| 3,706,304 | 12/1972 | Sisler | 73/80 |
| 3,911,903 | 10/1975 | Gee et al. | 128/2 T |

FOREIGN PATENT DOCUMENTS 1652057  4/1971  U.S.S.R. ............................. 128/2.05 D

OTHER PUBLICATIONS

Darling, R. C. et al., "Quantitative Segmental Pulse Volume Recorder: A Clinical Tool", Surgery V72 #6, Dec. 72 pp. 873-887.

Primary Examiner—Robert W. Michell
Assistant Examiner—Francis J. Jaworski
Attorney, Agent, or Firm—Charles E. Temko

[57] ABSTRACT

An improved ocular plethysmograph for use in conjunction with known pulse volume recorders, and offering increased performance and simplicity as well as lower cost of manufacture. The device employs a means whereby a large DC pressure signal is cancelled across a very sensitive DC pressure transducer employed to detect directly the tiny pressure fluctuations resulting from minute volume plethysmic changes of the human ocular globe. The means employed provides secondary advantages in use.

1 Claim, 1 Drawing Figure

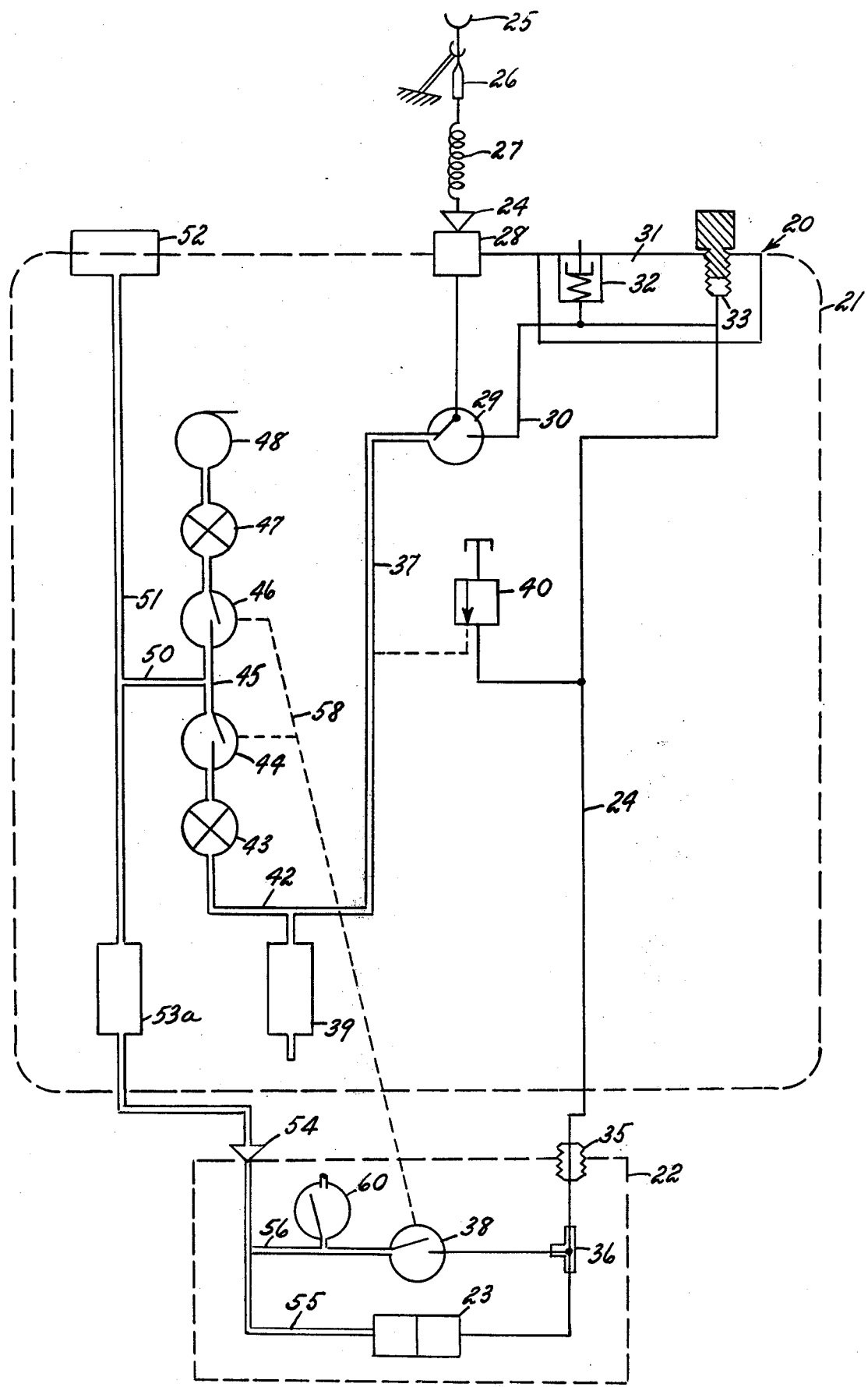

OCULAR PLETHYSMOGRAPH

BACKGROUND OF THE INVENTION

The known prior art includes a quantitative segmental pulse volume recorder employed as a clinical tool.[1] This device is adapted to obtain hemodynamic data in terms of pulse volume amplitude, pulse contour, and limb pressure, usable in pre-operative, operative and post-operative applications to provide a measure of the functional severity of occlusive diseases, as well as an objective base line for later comparisons. The known device includes a plurality of selectively applied pneumatic cuffs which are applied to portions of the body of a patient in areas of palpable pulses.

(1) See: Quantitative Segmental Pulse Volume Recorder, SURGERY, St. Louis, Vol. 72, No. 6, pp. 873–887; December 1972; copyright 1972, the C. U. Moody Co.

The nature of ocular plethysmography forms no part of the present disclosure, except as insofar as to describe the operation of the disclosed embodiment. A comparable device is disclosed in U.S. Pat. No. 3,911,903, granted Oct. 14, 1975 to W. Gee et al.

The practice of ocular plethysmography implies the use of an ocular plethysmograph in order to measure the minute volume fluctuations of the ocular globe and at various levels of internal, time-average pressure within the globe. The internal pressure is changed by varying suction applied to a small eye cup of approximately 12mm diameter attached (by the suction) directly to the sclera of the eye. An empirical correlation between the vacuum in the cup (of a peculiar, arbitrary form) and the pressure within the ocular globe has been established by Galin et al.[2], and by Gee et al[3] independently. In the disclosed device, this correlation is incorporated into the dial of an "ocular pressure" gauge, which is actually a vacuum gauge reading negative gauge pressure in the eye cup. At low vacuums, of the order of 50mmHg, the ocular pulse may be recorded with a properly configured system that has the necessary sensitivity (of the order of $0.1mm^3$) to resolve fluctuations of the ocular globe. In addition, the vacuum on the ocular globe may be increased until the ocular pulse disappears from the output of the plethysmograph. The ocular pressure at which the pulse disappeared may be interpreted as the systolic pressure of the ocular pulse. The medical significance of a recording of the ocular pulse and its systolic pressure is beyond the scope of the present disclosure.

(2) Galin, M. A.; Bara, I.; Best, M.: The Nature of the Ocular Pulse. HEADACHE, 9: 112–118, 1969.
(3) Gee, W. et al: Ocular Pneumoplethysmography in Carotid Artery Disease. MED INSTRUMENTATION, 8: 244–248, 1974.

SUMMARY OF THE INVENTION

Briefly stated, the invention contemplates the provision of an improved ocular plethysmograph of the class described characterized by major structural improvements which significantly lower the cost of manufacture of the device, allow increased facility in operation, greater accuracy in observed readings, and improved comfort to the patient. As contrasted with prior art devices, the pressure transducer is located a substantial distance from the eye of the patient, and is connected to the eye cup by a length of light weight tubing, thereby eliminating the necessity of suspending the transducer immediately over the eye of the patient. The DC vacuum signal transducer includes means for automatically balancing the same upon the occurrence of substantial shift in pressure, thereby preventing the possibility of damage, changes in calibration and zero shifts. This is accomplished by the provision of a pneumatic valve that opens to shunt together the two sides of the transducer every time the operator commands a change in vacuum, either negative or positive. Means is also provided to minimize spurious signals on the recorded trace as a result of vacuum slewing. The ocular line is provided with a safety disconnect device which protects the eye of the patient in the case of inadvertent impact by the operator with the boom supporting the signal line, or unanticipated movement by the patient. Calibration and gain controls are provided to permit standardization of the output traces, thereby removing any necessity for the operator to ascertain the gain employed for a given trace. An ocular pressure read-out is provided, which is independent of the trace for continuous monitoring.

BRIEF DESCRIPTION OF THE DRAWING

In the drawing, the single FIGURE is a schematic diagram showing the mechanical components of an embodiment of the invention.

DETAILED DESCRIPTION OF THE DISCLOSED EMBODIMENT

In accordance with the invention, the device, generally indicated by reference character 20 is illustrated in the drawing as incorporated into first and second modules 21 and 22, respectively. In the preferred form, the second module may be part of an existing apparatus having a pressure volume tranducer 23 employed for other diagnostic purposes. In the alternative, the device may be formed as a single module including the tranducer.

Extending outwardly of the first module 21 is an ocular line assembly 24 consisting of an eye cup 25, a safety disconnect means 26, a suitable length of tubing 27, and a port fitting 28 communicating with an ocular line valve 29. It will be observed that in the drawing certain vacuum lines which communicate with the reference side of the transducer 23 are drawn in double lines, while those communicating with the ocular side of the transducer have been designated by single lines. It is to be understood that both schematic representations, in fact, represent rigid or flexible pneumatic tubing.

Referring to the valve 29, a first line 30 leads to a gain-calibrate assembly 31 of known type, including a first element 32 including resilient means communicating with the atmosphere, and an adjustable chamber 33, the function of the assembly being to calibrate pulse volume changes for use with a recorder of known type (not shown). Such recording device is similar to those used in electrocardiagraph machines operating in the DC mode. During operation, calibration is preferably adjusted so that 1.0mm Hg change in vacuum provides a 20mm. deflection on the recording device.

From the assembly 31, an ocular signal line 24 extends to a fitting 35 on the casing of the second module 22. Communication from the fitting runs to a "T" connection 36, branches of which communicate with the ocular signal side of the transducer, and with a shunt valve 38. A relief valve 40 interconnects the ocular signal side and reference side of the device for returning ocular signal vacuum pressure to atmospheric pressure.

Extending from the valve 29 is a reference side line 37 communicating with the atmosphere through a filter 39. A second portion 42 thereof establishes communication in series with a vacuum decrease restriction means 43, a vacuum decrease control valve 44, a "T" connector 45, a vacuum increase control valve 46, a vacuum increase resistor 47 and a vacuum pump 48. The pump 48 is preferably equipped with a safety valve preventing it from drawing more than 300mm Hg. of vacuum.

A branch line 50 communicating with the connection 45 leads to another line 51, one end of which communicates with an ocular pressure gauge 52, and another segment 53 of which communicates through a pneumatic capacitor 53a to a port 54 in the second module 22. Extending from the port are reference side connections 55 and 56 to the transducer 23 and transducer shunt valve 38. The mechanical linkage 58 existing between the pressure control valves 43 and 46 and the shunt valve 38 cause the shunt valve to open each time one of the valves 44–46 is adjusted. Thus, with a sudden increase or decrease in vacuum pressure, the pressure differential existing on either side of the transducer diaphragm is immediately adjusted, preventing improper reading and/or damage to the diaphragm.

In addition to the above structure, which will maintain the shunt valve open during the entire period when the vacuum is changing, a protective circuit, including a valve 60 continuously examines the output signal of the transducer against a preset limit, to open the shunt valve anytime the change in pressure across the transducer approaches the mechanical operating limit of the transducer. Hence, leaks which sometimes occur in either the ocular signal circuit or the reference circuit (on the opposite side of the transducer) and which will cause the DC level of the vacuum to change with time, automatically shunt the transducer.

For example, assume that there is a minute leak in the ocular signal line which causes the eyecup vacuum to drift slowly while the operator is observing the ocular pulse on a strip chart recorder monitored by the output of the transducer. The ocular pressure gauge 52 will not record the drift because the gauge is located on the reference side of the transducer. Once the change in pressure across the transducer builds up to the order of plus or minus 7mm Hg, the shunt valve is automatically opened to cancel this DC bias. At the same time, the ocular signal line is brought back into pressure equilibrium with the reference side of the transducer, so that the ocular pressure gauge now does read the vacuum in the eye cup.

The mechanical linkage between the pressure control valves and the shunt valve may be substituted by suitable electronic controls (not shown) of well known type, which permit more instantaneous operation.

As contrasted with other devices known in the art, a feature of the present invention is the ability to locate the pressure transducer in a remote location relative to the eye cup. Rather than using a liquid-filled ocular signal line, which necessitates placing the pressure transducer in close proximity to the eye of the patient, by designing the vacuum line to keep the internal volume thereof within reasonable limits, it is possible to have only the ocular line and eye cup in the area of the patient supported by a very light boom near, but not necessarily directly above, the eye of the patient. Thus, a source of anxiety to the patient is eliminated. It has been determined empirically, that by maintaining the internal volume of the ocular signal circuit below 2000mm$^3$, the circuit will maintain sufficient sensitivity consistent with the resolution required for a change in volume occurring with each pulse, which is of the order of 0.1mm$^3$.

Attaining this small volume is difficult, especially since the ocular signal line is of the order of 2 meters in length, and must contain valves, connectors, eye cup, calibration volumes, etc. as well as the signal tubing. While the internal volume of the tubing is a large part of the total, it cannot be effectively reduced below a certain minimum diameter; otherwise, the higher frequency components of the ocular pulse are not transmitted from the eye to the pressure transducer diaphragm.

Many design features have been incorporated in order to minimize the ocular signal line volume. The most important are the placing of all vacuum controls on the reference (and non-volume-critical) side of the transducer, and placing the vacuum indicating gauge (ocular pressure gauge) on the reference side of the transducer.

I wish it to be understood that I do not consider the invention limited to the precise details of structure shown and set forth in this specification, for obvious modifications will occur to those skilled in the art to which the invention pertains.

I claim:

1. An improved ocular plethysmograph comprising: a vacuum generating pump, a vacuum cup positionable in direct contact with the sclera of the eye, a flexible vacuum line interconnecting said cap and said pump, means for incrementally adjusting the degree of suction applied to said vacuum cup, a pneumatic DC transducer including a diaphragm, means for maintaining a reference vacuum pressure on one side of said diaphragm, means in series with said flexible vacuum line communicating with the other side of said diaphragm, whereby instantaneous pressure differentials existing between the sides of said diaphragm will cause a corresponding DC signal output from said transducer; automatically actuated pneumatic valve means for instantaneously shunting together said sides of said transducer upon manual adjustment of said vacuum adjustment means beyond predetermined limits; and linkage means interconnecting said first mentioned means and said pneumatic valve means, whereby the differential pressure existing on said transducer is constantly maintained between said predetermined limits.

* * * * *